United States Patent
Chung et al.

(10) Patent No.: US 8,048,136 B2
(45) Date of Patent: Nov. 1, 2011

(54) PHOTOTHERAPY DEVICE

(75) Inventors: Dong-Chune Christopher Chung, Dublin, CA (US); Abraham John Totah, San Carlos, CA (US); Wesley Chung Joe, Mountain View, CA (US); Edmond Ming Wai Chiu, San Francisco, CA (US); David John Brude, Milpitas, CA (US); Bryan Patrick Flaherty, Half Moon Bay, CA (US); William Loyd Mince, Menlo Park, CA (US)

(73) Assignee: Natus Medical Incorporated, San Carlos, CA (US)

( * ) Notice: Subject to any disclaimer, the term of this patent is extended or adjusted under 35 U.S.C. 154(b) by 758 days.

(21) Appl. No.: 11/423,694

(22) Filed: Jun. 12, 2006

(65) Prior Publication Data
US 2007/0088410 A1 Apr. 19, 2007

Related U.S. Application Data

(60) Provisional application No. 60/689,339, filed on Jun. 11, 2005.

(51) Int. Cl.
*A61N 5/06* (2006.01)
(52) U.S. Cl. ............................................. 607/91; 607/88
(58) Field of Classification Search .............. 607/88–91; 606/8–12; 362/600, 602–608, 127, 130, 362/131
See application file for complete search history.

(56) References Cited

U.S. PATENT DOCUMENTS

| | | | |
|---|---|---|---|
| 4,542,547 A | 9/1985 | Sato | |
| 4,827,763 A | 5/1989 | Bourland et al. | |
| 4,907,132 A | 3/1990 | Parker | |
| 5,339,223 A | 8/1994 | Kremenchugsky et al. | |
| 5,400,425 A | 3/1995 | Nicholas et al. | |
| 5,792,214 A | 8/1998 | Larsson et al. | |
| 5,901,391 A * | 5/1999 | Kato | 5/666 |
| 5,917,180 A | 6/1999 | Reimer et al. | |
| 5,944,748 A * | 8/1999 | Mager et al. | 607/88 |
| 6,016,215 A | 1/2000 | Byker | |
| 6,045,575 A | 4/2000 | Rosen et al. | |
| 6,290,713 B1 * | 9/2001 | Russell | 607/88 |
| 6,402,681 B1 | 6/2002 | McDonough et al. | |
| 6,494,901 B1 | 12/2002 | Doty | |
| 6,560,804 B2 | 5/2003 | Wise et al. | |
| 6,596,016 B1 | 7/2003 | Vreman et al. | |
| 6,811,563 B2 * | 11/2004 | Savage et al. | 607/88 |
| 6,872,220 B2 | 3/2005 | Williams et al. | |
| 7,077,544 B2 | 7/2006 | Parker | |
| 7,147,653 B2 * | 12/2006 | Williams et al. | 607/88 |
| 7,330,127 B2 | 2/2008 | Price et al. | |
| 2003/0009205 A1 * | 1/2003 | Biel | 607/88 |
| 2004/0039428 A1 * | 2/2004 | Williams et al. | 607/88 |
| 2004/0068305 A1 | 4/2004 | Bansal et al. | |
| 2005/0149149 A1 | 7/2005 | Chung et al. | |
| 2006/0038192 A1 | 2/2006 | Williams | |
| 2006/0100675 A1 | 5/2006 | Gardner | |
| 2007/0100400 A1 | 5/2007 | Chung et al. | |

* cited by examiner

*Primary Examiner* — Ahmed Farah
(74) *Attorney, Agent, or Firm* — Shay Glenn LLP

(57) ABSTRACT

A phototherapy system having a rigid support surface adapted to support a patient without substantial deformation; a light source disposed so as to transmit light through the support surface; and a mask adapted to permit light transmission from the light source through a first portion of the support surface and to limit light transmission from the light source through a second portion of the support surface.

23 Claims, 9 Drawing Sheets

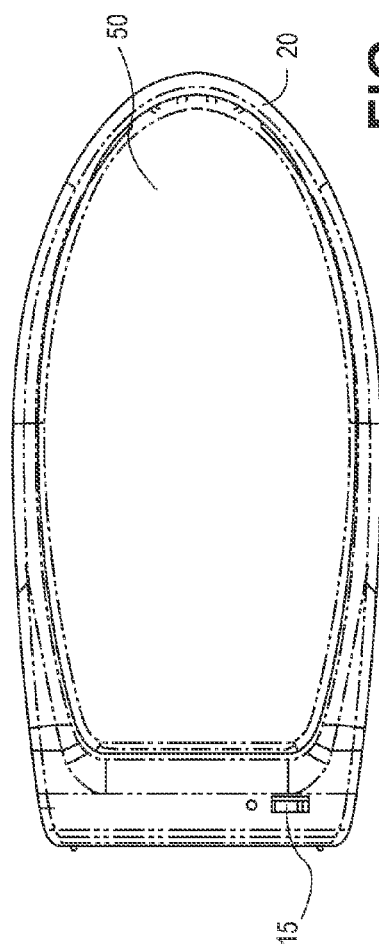
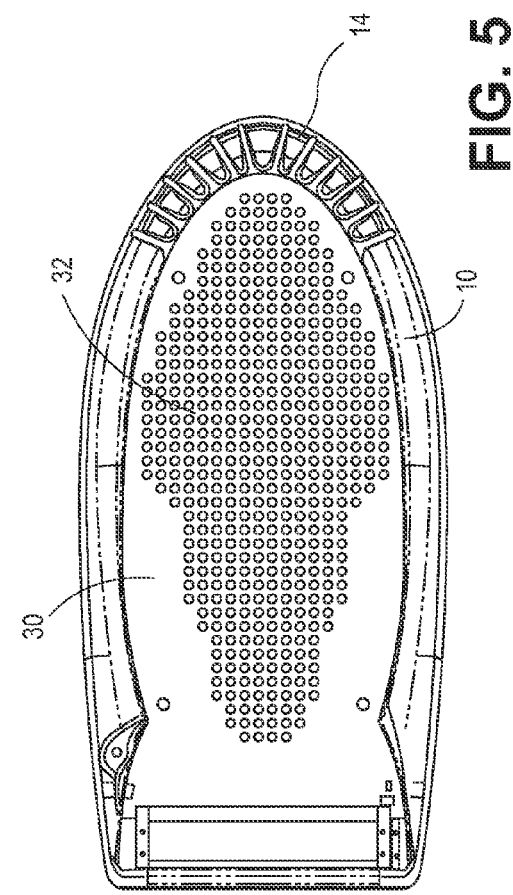

PHOTOTHERAPY DEVICE

CROSS-REFERENCE

This application claims the benefit of U.S. Provisional Application No. 60/689,339, filed Jun. 11, 2005, which is incorporated herein by reference in its entirety.

BACKGROUND OF THE INVENTION

This invention relates to devices for the phototherapeutic treatment of illness and diseases.

Phototherapy is a promising clinical tool for the treatment for many conditions, including seasonal affective disorder, bulimia nervosa, herpes, psoriasis, sleep disorders, acne, and skin cancer.

Phototherapy is especially promising as a treatment for hyperbilirubinemia, a common condition affecting about 60% of all newborns. Hyperbilirubinemia is caused by the accumulation of excess bilirubin in the blood of the infant. This excess bilirubin turns the skin and sclera a characteristic yellow color. If left untreated, extreme cases of hyperbilirubinemia can result in neurological insult (kernicterus) or even death. A common treatment for hyperbilirubinemia is phototherapy, in which the infant is exposed to light in a range corresponding to the absorption spectra for bilirubin (blue-green, 400-550 nm). This light energy changes the form of the bilirubin to a different isomer that is more readily eliminated by the body.

Phototherapeutic light can be provided from above (by using an overhanging panel), from below (by using an illuminated pad or bed), from all sides (by using a phototherapeutic garment or blanket), or combinations thereof. Prior phototherapy systems are described, e.g., in Kremenchugsky U.S. Pat. No. 5,339,223; Rosen U.S. Pat. No. 6,045,575; Russell U.S. Pat. No. 6,290,713; Larsson U.S. Pat. No. 5,792,214; Nicholas U.S. Pat. No. 5,400,425; Vreman U.S. Pat. No. 6,596,016; Williams U.S. Pat. No. 6,872,220; Williams U.S. Pub. No. 2004/0039428; Bansal U.S. Pub. No. 2004/0068305; and Gardner U.S. Pub. No. 2006/0100675.

Regardless of the technique used, it is important to limit the "leakage" of phototherapeutic light; that is, phototherapeutic light not absorbed by the patient. Ideally, all the emitted light is absorbed by the patient, however a significant percentage of the phototherapeutic light never strikes the patient. This is especially true using overhanging panels and illuminated pads or beds. This leakage, or extraneous light, is simply wasted, and some individuals report nausea or discomfort from prolonged exposure to leaked phototherapeutic light. Systems and devices are therefore needed to reduce the amount of leaked or extraneous light during phototherapy.

In addition, phototherapy systems, particularly for infants, should be safe, effective and easy to use. For example, any extraneous heat generated a phototherapy system should be safely handled. Providing a comfortable and hygienic environment for the patient is also important.

SUMMARY OF THE INVENTION

The present invention is a device that provides phototherapeutic light from below a patient. The device includes a phototherapeutic light or lights, and a structure or structures for holding the light(s) and for supporting the subject (typically an infant). The device also includes means for reducing or minimizing the dispersion of extraneous light.

One aspect of the invention provides a phototherapy system having a rigid support surface adapted to support a patient without substantial deformation, a light source (such as, e.g., a plurality of light-emitting diodes (LEDs)) disposed so as to transmit light through the support surface, and a mask adapted to permit light transmission from the light source through a first portion of the support surface and to limit light transmission from the light source through a second portion of the support surface. The light source may comprise a plurality of light sources operating at a plurality of colors. The mask may be further adapted to block or attenuate light transmission from the source through the second portion. The mask may include a thermochromic material, a patient location sensor, and/or a fluid-filled pad.

In some embodiments, the invention includes a patient orientation element, e.g., a visible shape in or on the support surface. In such embodiments, the light source (e.g., LEDs) may have a substantially non-uniform concentration with respect to the orientation element. For example, the patient orientation element may have a head area adapted to orient the head of the patient with respect to the support surface. The light source may comprise a plurality of LEDs having a concentration greater near the head area than in another area of the orientation element.

In some embodiments, the phototherapy system also includes a cooling assembly adapted to control heat within the system. The cooling system may include, e.g., a fan and/or a temperature sensor.

In some embodiments, the phototherapy system has a light level controller, such as a temperature sensor.

Some embodiments of the invention have a mattress adapted to be disposed between the patient and support surface and to transmit light from the support surface to the patient. The system may also include a mattress cover disposed over at least a portion of the mattress and adapted to transmit light.

In some embodiments, the phototherapy system also includes a pressure-sensitive switch adapted to control the light source.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4 is a top view of the embodiment shown in FIG. 2.

FIG. 5 is a top view of the embodiment shown in FIG. 2 with the base cover removed.

DETAILED DESCRIPTION

One aspect of the invention is a phototherapy system which includes a rigid support surface adapted to support a patient without substantial deformation, a light source disposed so as to transmit light through the support surface, and a mask adapted to permit light transmission from the light source through a first portion of the support surface and to limit light transmission from the light source through a second portion of the support surface. The system preferably reduces or minimizes the amount of leakage of phototherapeutic light from the system so that the light is primarily absorbed by the patient while reducing light exposure to others. In some embodiments the system can minimize or reduce leakage by responding to the patient's position or orientation on the system, while in other embodiments the minimization or reduction is independent of the position of the patient. The system may be used in the treatment of hyperbilirubinemia or other conditions treatable using phototherapy.

Figure 1:
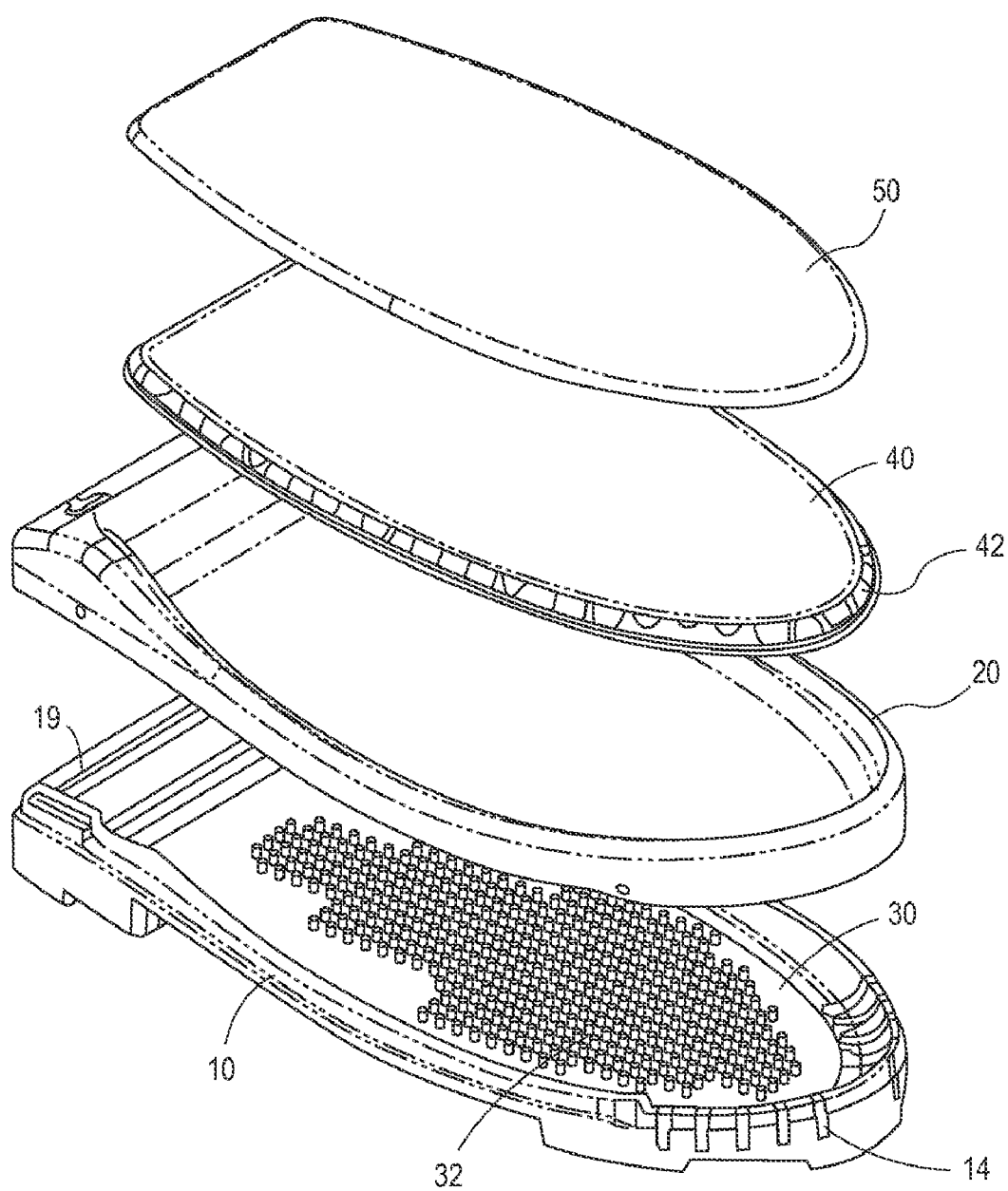
FIG. 1 is an exploded perspective view showing components of an exemplary embodiment of the phototherapy system.

FIG. 1 is an exploded view of the system and illustrates the general components of an exemplary embodiment of the system, wherein rigid support structure comprises base 10 and base cover 20, which is adapted to be placed on top of base 10. Rigid support structure as shown also comprises mattress 40 adapted to be placed on base cover 20, and mattress cover 50 adapted to be placed on mattress 40. A patient [not shown] would be positioned on top of mattress cover 50 during phototherapy. Base 10 includes light supporting structure 30 to which light source 32 is coupled.

Figure 2:
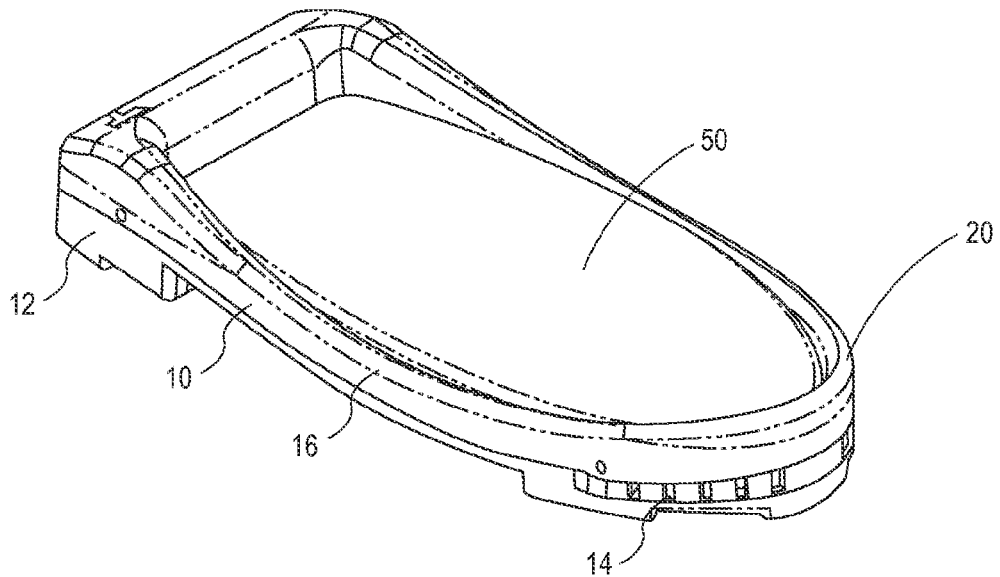
FIG. 2 is a perspective view of an inactive embodiment of the present invention.
Figure 3:
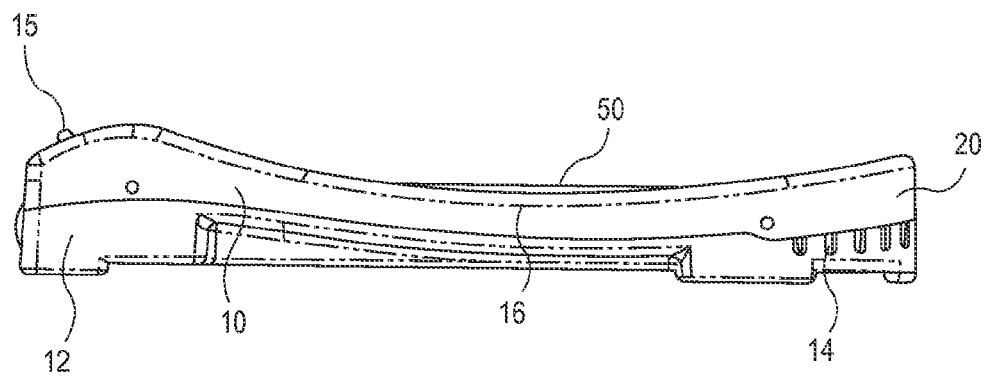
FIG. 3 is a side view of the embodiment shown in FIG. 2.

FIG. 2 illustrates an embodiment showing the assembled components from FIG. 1. FIGS. 3 and 4 show a side view and top view, respectively, of the system of FIG. 2. FIG. 5 shows the top view of FIG. 4 with base cover 20 removed to show a top view of base 10, including light supporting surface 30 and light source 32.

In preferred embodiments the rigid support structure includes a base. Generally, the base provides support for additional components of the system, as well as for a patient receiving phototherapy. Base may be of any suitable size and shape, however, it will be of sufficient size to support at least an infant. The base and/or base cover, as described below, may have walls 16 as shown in FIGS. 2 and 3 that provide support for the infant during therapy and may also prevent the patient from rolling off of the device. The base is preferably made of any material that can provide support to a patient and to the additional system components without substantial deformation. Exemplary materials include without limitation, plastic or metal, or any combination of materials.

The base may also comprise additional system components including, without limitation, a power supply, a cooling assembly including fans, vents 14 as shown in FIGS. 2, 3 and 5, and/or other cooling elements to cool the system, a pedestal 12 as shown in FIG. 3 to provide additional support for the system, and other electrical components such as, without limitation, a light level controller, which is discussed in detail below.

The rigid support surface may also include a base cover which is adapted to be coupled to the base. The base cover may be coupled with the base by any known method, including screws, snap together pieces, or any other suitable fastening mechanism known in the art. In some embodiments the base cover can act to protect the system components housed within the base, such as the light source or the power supply. The base cover may, additionally, comprise system components such as, without limitation, a power switch 15, manual power level controller as described below, or any of the other system components that may be housed in the base described herein. The base cover may be optional, for example, when a pressure activated light source is used as described below.

The system of the present invention includes a light source which provides the phototherapy to a patient. In some embodiments the light source comprises a plurality of LEDs. In preferred embodiments the light source comprises a plurality of LEDs that emit light in the range of about 400 to about 550 nm. In more preferred embodiments the LEDs emit blue light in the range of about 450 to about 470 nm, which matches the peak absorption at which bilirubin absorbs light, and is thus considered to be the most effective treatment for hyperbilirubinemia. Any suitable number or position of LEDs may be used.

Alternatively, other types of LEDs, lasers, or laser diodes also may be used. The light source may be multicolored LEDs, or the light source may comprise a plurality of light sources operating at a plurality of colors, such as in the Natus neoBLUE LED Phototherapy System®. The light source may comprise blue and yellow LEDs. In such embodiments, generally, the blue LEDs provide the treatment light, and the yellow LEDs provide color balance, making it easier on a caregiver's eyes. For the treatment of neonatal hyperbilirubinemia, the preferred treatment color of LEDs is blue, although green LEDs also may be effective. The treatment of other conditions may require differently colored LEDs. For example, herpes may be most effectively treated by red LEDs, seasonal affective disorder may be treated by white or yellow LEDs, and psoriasis may be treated by ultraviolet LEDs. Other light sources can be used, including fluorescent lights. The condition being treated and the light source used for the treatment may vary while carrying out a purpose of the invention to prevent or minimize exposure of phototherapeutic light to those other than the patient.

The intensity or power level of the lights throughout the light source may also vary depending on the likelihood that the patient's body will be exposed to an area of the system. Depending on the size of the patient, for example, the intensity of the lights throughout the light source can be adjusted to prevent "leakage" of phototherapeutic light, that is, light that is emitted and not absorbed by the patient. For example, if an infant of smaller than average size requires phototherapy, the intensity of lights towards the periphery can be decreased while maintaining the normal intensity of the lights near the center, as a small infant may require less light than a baby of, for example, textbook normal size. The intensity may be adjusted manually by a light level controller housed preferably within the base or base cover, or the system may have a temperature sensor which detects, for example, overheating, and can automatically adjust the intensity accordingly. The system may comprise a device capable of making the plurality of lights separately addressable so that they may be selectively illuminated in a particular pattern to achieve a particular therapeutic result. The system may have a non-uniform concentration of lights throughout the light supporting structure, the power of which may be simultaneously varied throughout the light source to achieve the desired light emission pattern. However, the system may also have a uniform concentration of lights throughout the light structure without departing from the intent of the invention.

The system includes any suitable interconnection technology to provide an electrical circuit among the power supply, the light source, power switch, cooling assembly, light level controller, and any other electrical component of the system described herein. For example, the system may also include a timer which can automatically shut off the light source after a desired exposure time. Electrical components are preferably housed within the base or base cover, but may additionally be housed within other system components as well.

This aspect of the system also comprises a mask adapted to permit light transmission from the light source through a first portion of the rigid support surface and to limit light transmission from the light source through a second portion of the support surface. The mask helps reduce the amount of emitted light exposed to individuals other than the patient.

FIG. 1 illustrates one exemplary embodiment of a mask of the present invention, where the light source 32 is shown with a non-uniform concentration of LEDs throughout the light supporting structure 30. The LED's are more concentrated near the center and rounded end of the rigid support structure, while less concentrated near the periphery, and even absent, near the straight end of the support surface. The light source may comprise a non-uniform concentration of LEDs because a patient's body may not uniformly cover the entire surface of the rigid support surface. The distribution or concentration of the LEDs may vary depending on the probability that a patient's body will cover a particular region. For example, as shown in FIG. 1, more surface area of the patient is likely to be positioned in the center and near the rounded end of the system than at the periphery and straight end of the system. The quantity or concentration of lights may therefore be greater in the center and near the rounded end. Fewer lights are therefore placed where there is less probability the patient's body will contact the system, such as near the straight end, where the subject's legs and feet may be positioned. The distribution of the light source can help conserve energy required by the system for the phototherapeutic treatment, as well as reduce the amount of emitted light to non-patients such as caregivers.

Figure 6:
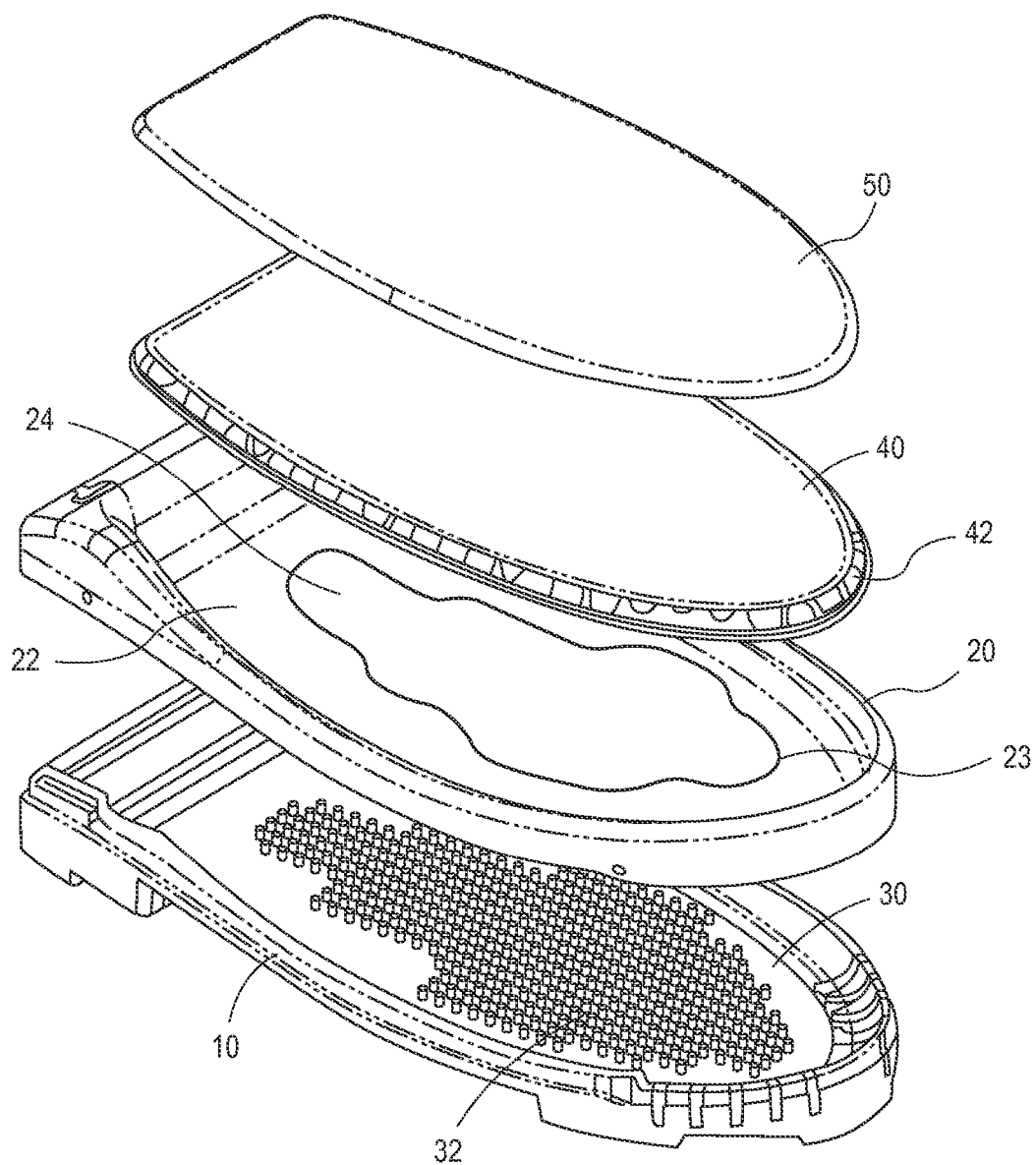
FIG. 6 illustrates an exemplary mask of the present phototherapy system.

FIG. 6 illustrates another exemplary embodiment of a mask of the phototherapy system. The mask 22 may be placed on top of base cover 20 as a separate structure or layer of the system such that mask 22 is positioned on top of transparent region 24 of base cover 20, or mask 22 can comprise a transparent region 24. When the mask comprises a transparent layer, the mask 22 may be a different layer than base cover 20, or base cover 20 may comprise mask 22. When the mask is distinct from the transparent region 24 and is a layer separate from base cover 20, it can take the form of a template that can be re-positioned on the base cover depending on the patient's location. Mask 22 can be formed by any method to limit the amount of light transmitted through the mask 22 from the light source. For example, mask 22 can be painted on the base cover 20. In FIG. 6 mask 22 limits the light transmitted through mask 22, while transparent region 24 permits light to be transmitted through transparent region 24 such that it is absorbed by a patient.

The interface between transparent region 24 and a mask 22 forms a transition zone 23 that may have substantially the same shape and position as the outline of the most peripheral lights in the light source 32. The transparent region 24 is positioned approximately above the light source 32, while the mask 22 is positioned approximately above the light supporting structure 30 where there is no light source. The light source may, however, be uniformly distributed throughout the light supporting structure, in which case the transition zone 23 would not have substantially the same shape and position of the outline of the most peripheral lights in the light source.

In some embodiments the mask substantially blocks light, particularly light emitted from the light source, from traveling through it rather than merely attenuating or diffusing the light. The transparent region permits light to transmit through the support surface in areas where a patient in likely to be positioned, while the mask helps limit the amount of emitted light that is exposed to others which is not absorbed by the patient. The mask may be any suitable material that substantially blocks light from traveling through it, such as without limitation, an opaque plastic material. In such an embodiment, a blanket or other cover also could be placed over the patient, thereby further blocking the transmission of extraneous phototherapeutic light into the environment. However, such a blanket might preclude simultaneous treatment with phototherapeutic light from above the patient.

In some embodiments the mask diffuses or attenuates light from the light source rather than blocks it completely. Attenuating includes, e.g., filtering certain colors, diffusing the light, or any other alteration of the light passing through the mask. Because a patient is more likely to be positioned in the center of the rigid support surface, he or she will be exposed primarily to undiffused phototherapeutic light, while onlookers will primarily be exposed to the diffused or attenuated light from the periphery. This will reduce the amount of exposure to non-patient persons such as caregivers.

In some embodiments the mask comprises a thermochromic material, such as ink or paint. Thermochromic material involves the use, e.g., of liquid crystal or leuco dye technology. After absorbing a certain amount of light or heat, the crystal or molecular structure of the pigment reversibly changes in such a way that it absorbs and emits light at different wavelengths than at lower temperatures. Once the thermochromic material absorbs heat it can become transparent. As used herein, thermochromic material can be used as a mask in the system, and once it absorbs heat from a patient's body through conduction, it can become transparent and allow light to pass through the transparent region. It should remain opaque at room temperature, but become transparent as it approaches body temperature.

Figure 7:
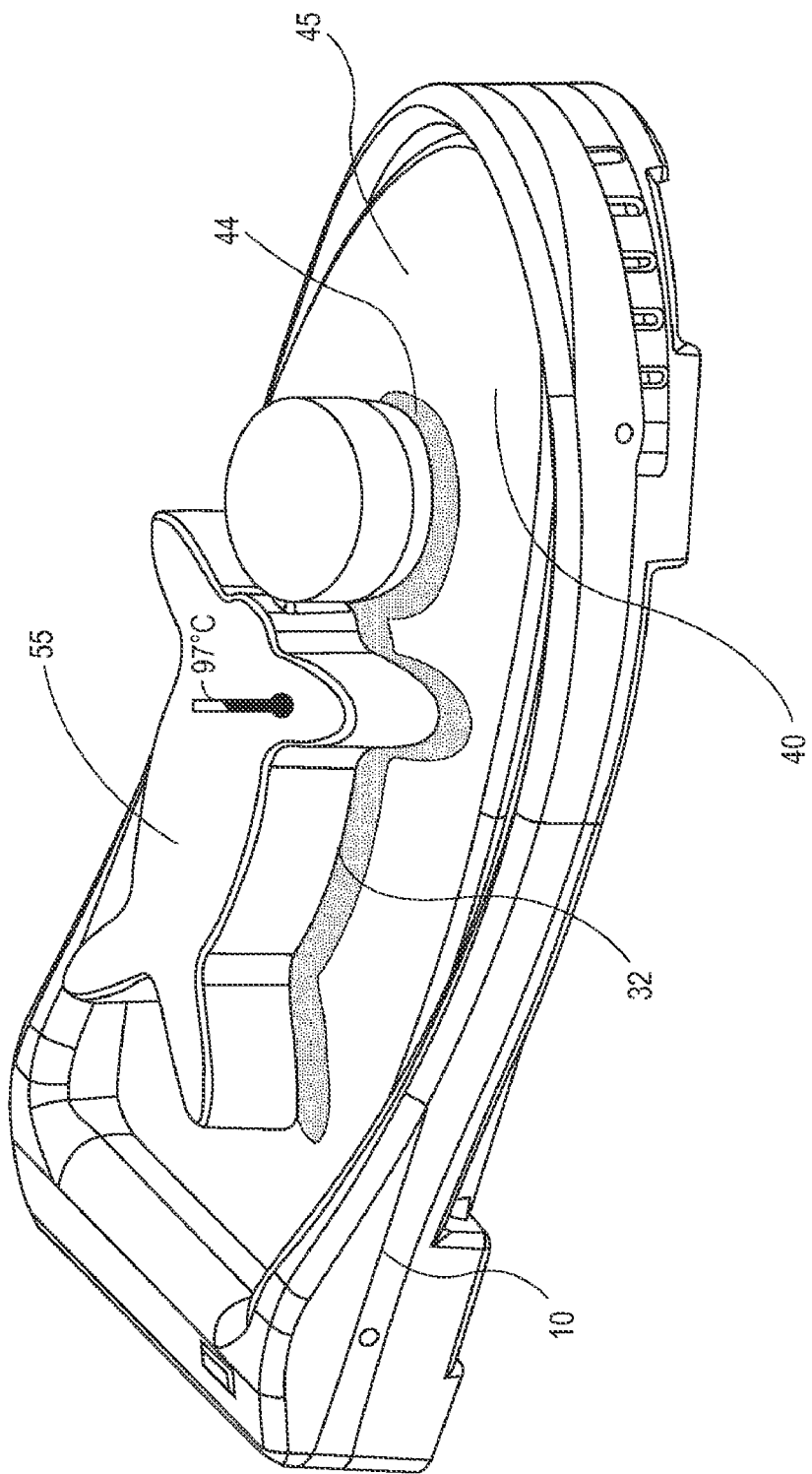
FIG. 7 show a perspective view of a phototherapy device according to an embodiment of the present invention, in which the mattress comprises a thermochromic paint [or ink].

FIG. 7 illustrates an exemplary embodiment where a mask comprises thermochromic material. Patient 55 is shown on mattress 40, which may or may not be covered with a mattress cover. In this embodiment, the mattress 40 is transparent and comprises a layer of thermochromic material. The thermochromic material can coat the mattress, or it may be a separately contained layer within the mattress. The thermochromic material may be present throughout the entire surface of one side of the pad, or it can be absent from areas of the mattress that will likely be covered by a patient's body. For example, there may be no need for thermochromic material in the center of the mattress as there is a high probability the patient's body will be located in the center and therefore the transparency of the mattress can be used to transmit light from the light source to the patient. Thermochromic material would not be necessary in this region.

In FIG. 7, thermochromic material that has been heated by the patient's body 55 due to heat transfer is shown as transparent heated thermochromic material 44, which permits light from the light source 32 to transmit through the transparent portion of the support surface, while opaque regions of the thermochromic paint that are at room temperature 45 block the light from light source 32. Only the light from below the patient is transmitted through the mattress, and the extraneous light, that which would otherwise be transmitted through the mattress and around the patient, is blocked by the opaque ink 45. Thus, the transparent heated thermochromic material allows phototherapeutic light to be substantially absorbed by the patient, while the opaque thermochromic material limits the amount of phototherapeutic light exposed to nonpatients.

The system may comprise a cooling assembly as described below to ensure that heat from the light source does not cause the thermochromic material to change color. In some embodiments a cooling assembly fan may be placed between the light source 32 and the mattress 40 or may be placed beneath the light source 32 in the base 10, providing airflow between the light source 32 and mattress 40.

Figure 8:
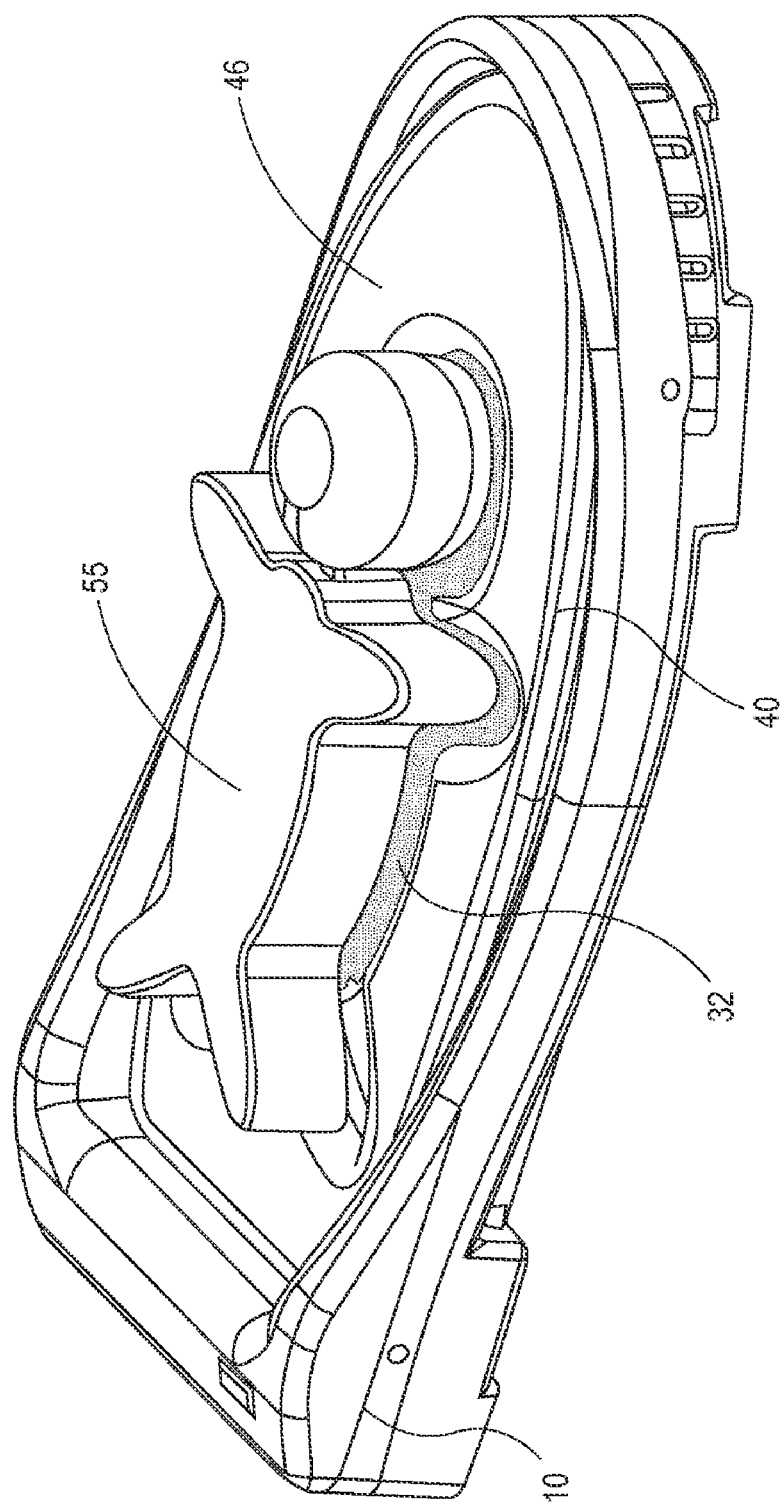
FIG. 8 depicts an embodiment of the present invention in which the mattress is filled with an opaque liquid or gel that is displaced by the subject's weight.

FIG. 8 illustrates an exemplary embodiment of the system where the mask comprises a fluid-filled pad or pouch. In FIG. 8 mattress 40 is a transparent pouch and is filled with an opaque liquid or gel 46. When patient 55 is placed on the mattress 40, the weight of the patient's body displaces the opaque fluid 46 from the area of the pouch underneath the patient's body, permitting light to selectively pass through only those transparent areas of the mattress 40 underneath the patient. Leakage of extraneous light is thereby reduced or even eliminated, and health care workers are less likely to feel discomfort from viewing the phototherapeutic light. The opaque liquid or gel may be, e.g., colored water, or water-based suspensions of solids.

The amount of opaque liquid or gel 46 that is inside the transparent mattress 40 is preferably great enough such that when the weight of the body displaces the liquid or gel, there are not any transparent pockets or bubbles that are not directly beneath the patient. In addition, however, the amount of liquid or gel in the transparent pouch is preferably not great enough such that the body weight can not displace enough of the liquid or gel to provide any transparent regions beneath the patient. This would prevent any light from the light source from being transmitted to the patient. Preferably when the patient is on the mattress 40, the liquid or gel in the pouch is displaced and exerts enough force on the outer edges of the mattress so that there are not any transparent regions that are not directly beneath the patient, while the area of the mattress directly below the patient is substantially transparent. Thus, the size of the transparent pouch and the volume of liquid or gel must be chosen to carry out the intent of the invention.

Another embodiment would include placing a substance such as paraffin in the pad that changes phase and color from, for example, opaque to transparent when warmed by the baby's body. Thus, the area underneath the infant would be clear, while other areas would remain opaque, similar to the thermochromic paint embodiment described above.

Another embodiment would include the use of a filter material, e.g., a pressure sensitive or pressure indicating film, which changes color and/or opacity when compressed by the baby's weight. Pressurex®, made by SPI, e.g., could by used as such a pressure sensitive or pressure indicating film to indicate the location of the patient.

In another embodiment of the system shown in FIG. 8, the transparent mattress 40 could contain two different substances, one which is opaque and the other transparent. The density and/or the viscosity of the two substances are selected so that the opaque substance would be displaced by the patient's weight while the transparent substance would remain substantially directly below the patient and not be displaced, thus permitting light from light source substantially directly beneath the patient to be transmitted through the mattress to the patient, while blocking other light from being exposed to others. The two different substances could each be liquids or gels.

In some embodiments the system comprises one or more patient location sensors. The sensor senses the location of the patient on the rigid support surface, communicates the location of the patient to a light level controller within the system, and the light level controller either directly or indirectly illuminates only those lights that correspond to locations substantially directly beneath where the patient is situated on the rigid support surface.

Figure 9:
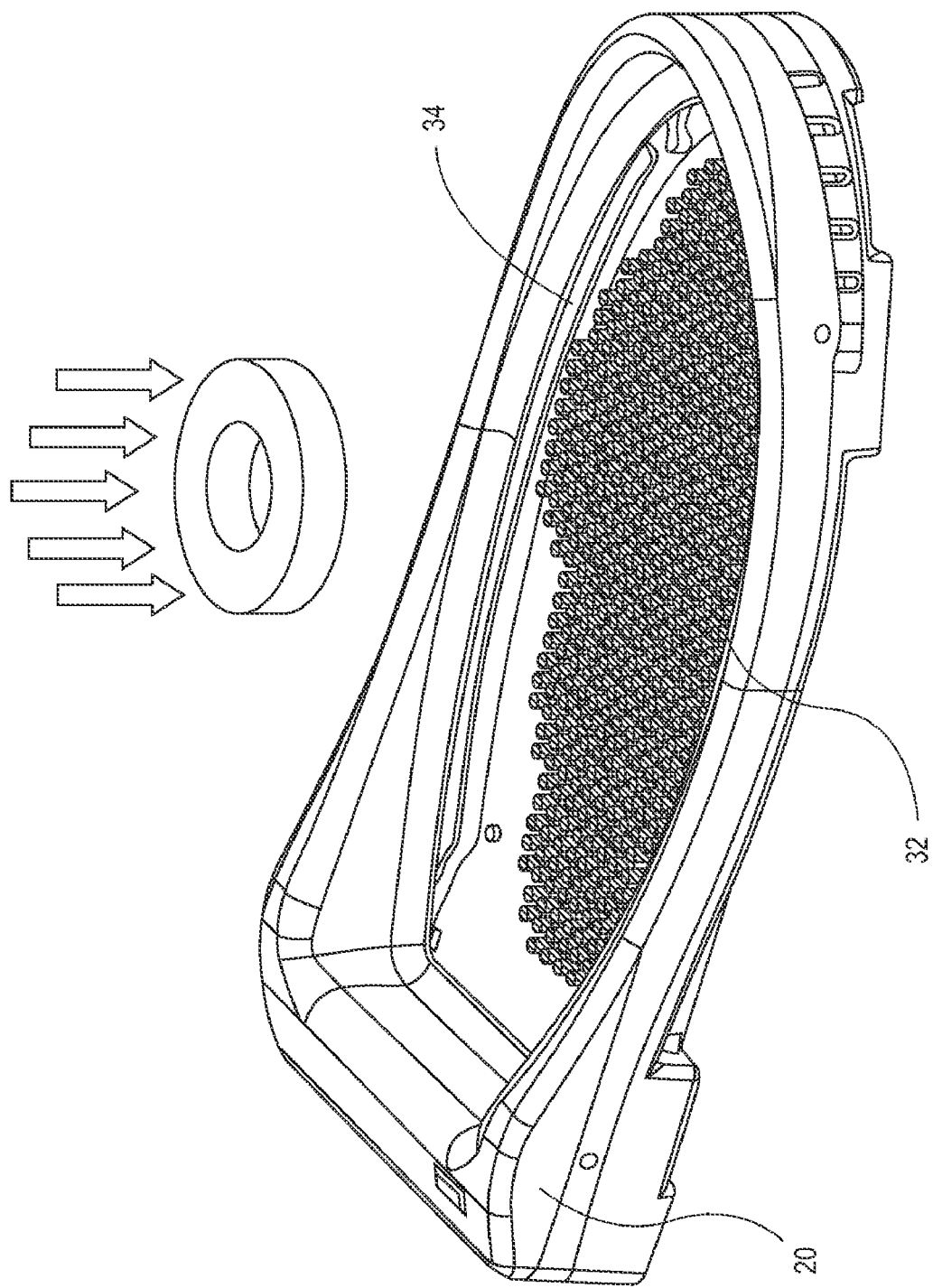
FIGS. 9 and 10 illustrate embodiments of the present invention in which the light source contains pressure sensitive switches that are activated by the patient's weight.
Figure 10:
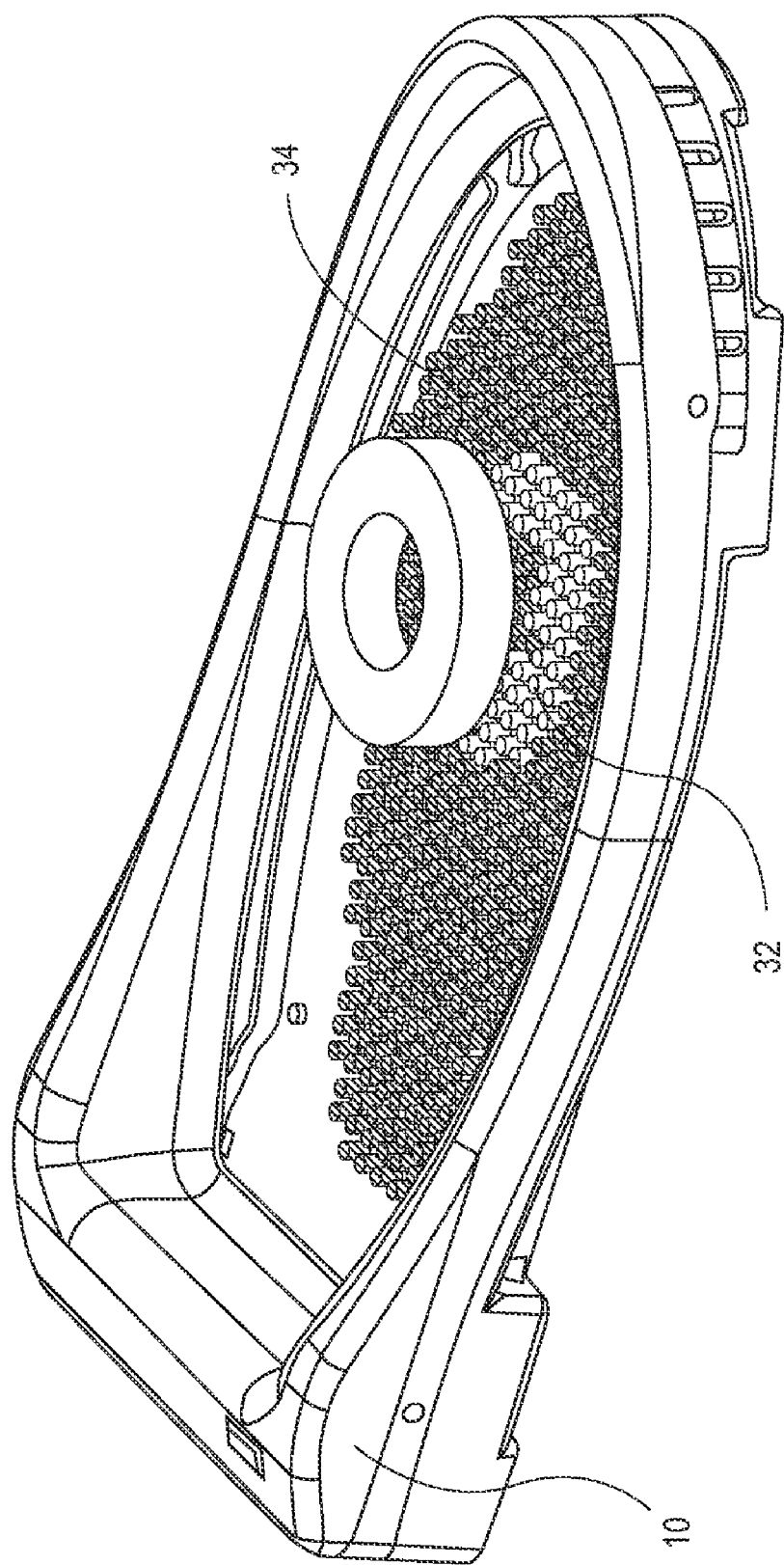

In some embodiments as shown in FIGS. 9 and 10 the patient sensor location comprises a pressure sensitive switch 34, and one or more lights in the light source 32 are controlled by a pressure sensitive switch associated with the light. Only when a patient's body activates the pressure sensitive switch is the light associated with that switch illuminated. Thus, only those lights that are underneath the patient's body will be illuminated, as illustrated in FIG. 10. In this embodiment, the mattress 40 is optional, but preferably allows light to pass through. To allow sufficient contact between the patient's body and the pressure sensitive switch, the mattress may be of such material such that the mattress does not prevent the patient from contacting the switches. If a mattress is not used, a transparent cover that allows the body to come into contact with the pressure sensitive switch is placed between the patient's body and the light source 32.

The rigid support surface may comprise a mattress 40 which can be placed above the base cover to provide comfortable cushioning underneath the patient. The mattress 40 may have filler material 42 as shown in FIG. 1. The rigid support surface may further comprise a mattress cover adapted to be disposed on the mattress, and which may be disposable to provide a clean and sanitary surface for the patient. The patient is preferably positioned on the mattress, or on the mattress cover if one is used, during the phototherapy treatment. The mattress should be capable of transmitting light from the light source 32 to the patient. However, the mattress 40 and/or its filling may have light diffusion properties.

The mattress 40 may also be concave to help ensure that the patient remains in place during the phototherapy session. The amount of filler material 42 may be adjusted within the mattress to help produce the concave region. For example, less filler material may be used near the center of the mattress to create a concave shape to the mattress. In addition, by placing less filler material near the center of the mattress, not only is a concave region created, but the region is also more transparent to light as there is less filler material, which enhances the amount of light that may be absorbed by the patient.

The mattress may serve a secondary purpose of diffusing the phototherapeutic light before it is absorbed by the patient, providing a more even exposure of light to the patient's skin than without a diffusive layer. The mattress can be made of polyester or polyurethane and/or other suitable materials. A weave or fabric can be placed on top of the mattress for the patient's comfort. A mattress cover may be fitted on top of the mattress, and this cover may be disposable. The cover may have light diffusion properties similar to the mattress.

The system is configured such that a blanket may be placed over a patient for warmth during phototherapy, or a blanket may be incorporated into the system. The system can also be used in conjunction with an overhead phototherapy system for additional exposure, for example, as is described in pending U.S. patent application Ser. No. 10/265,970 (Publication No. 2004/0068305) or Ser. No. 10/651,906 (Publication No. 2005/0149149), both of which are incorporated herein by reference in their entirety.

Figure 11:
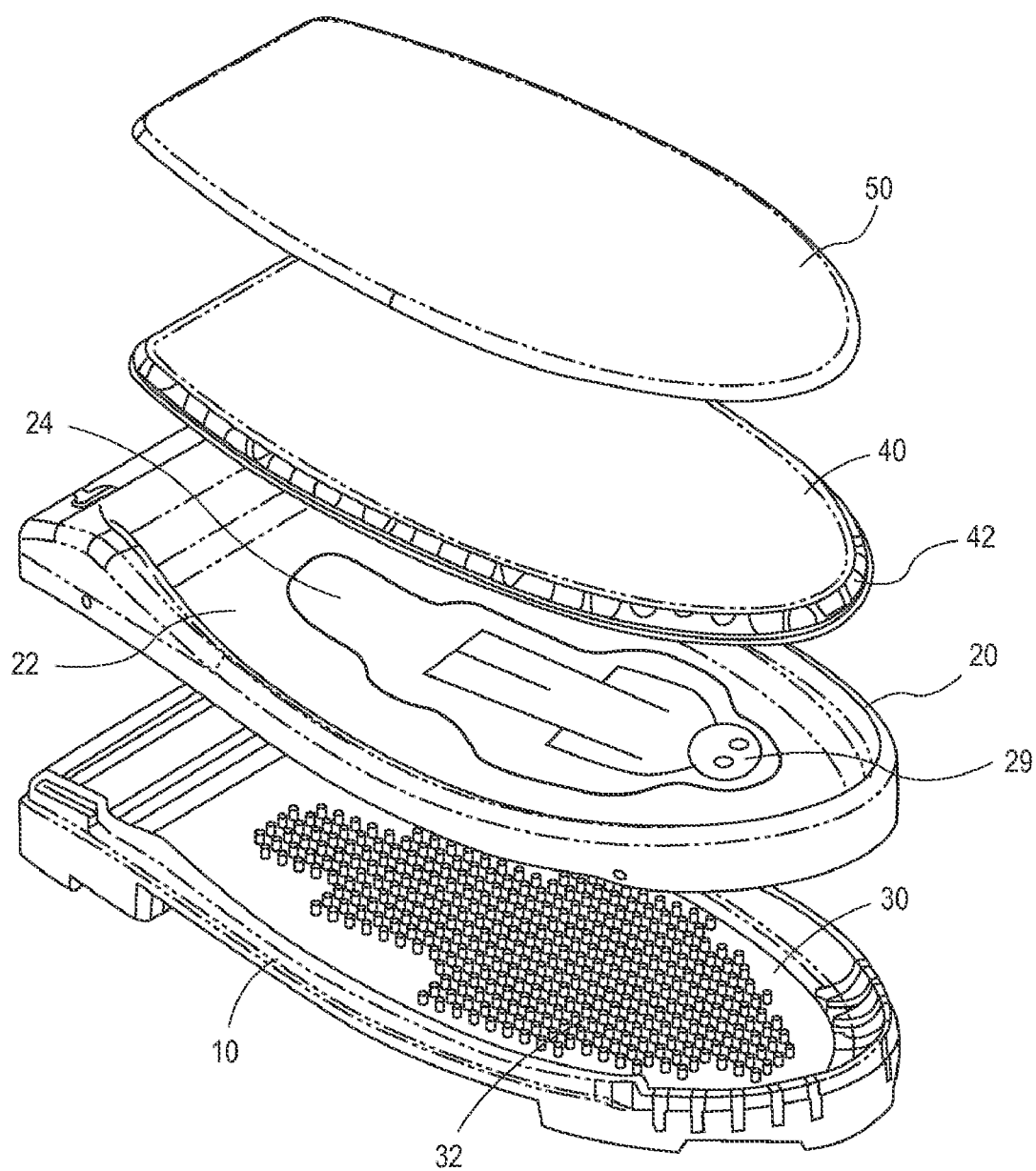
FIG. 11 shows a patient orientation element of the phototherapy system.
Figure 7:
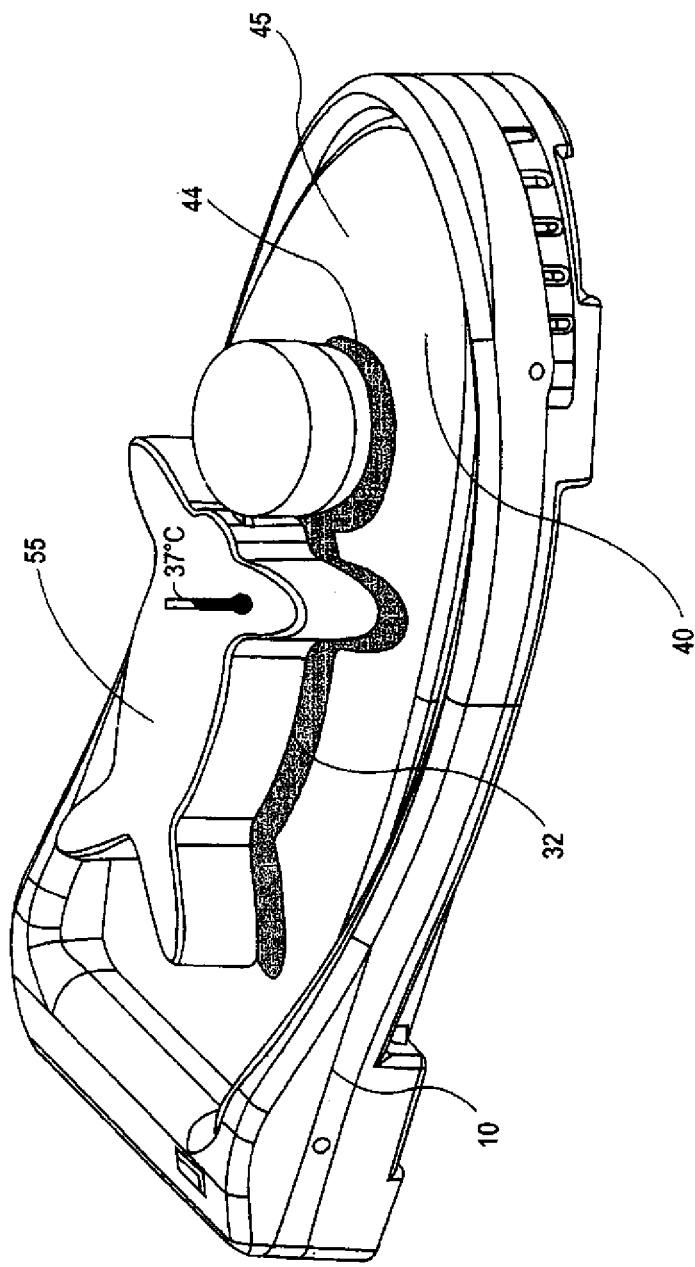

In some embodiments the phototherapy system of the present invention comprises a patient orientation element. The orientation element assists a caregiver in placing a patient in the right position and/or orientation on the rigid support surface. As shown in FIG. 11, patient orientation element comprises an illustration of a patient 29 to illustrate the proper orientation of the patient on the support surface. The illustration shows that the patient's head should be placed near the rounded end of the system, while the legs and feet should be placed towards the straight end. The orientation element also shows the patient should be placed in a supine position, or placed on the patient's back. The patient orientation element can be any type of indicator, for example, visual, tactile, or audio. The orientation element in FIG. 11 is shown on the base cover 20, but may be on a different part of the system, for example, imprinted on the mattress or mattress cover. The LEDs are shown having a substantially non-uniform concentration with respect to the orientation element and the concentration of LEDs is greater near the rounded end of the system.

In preferred embodiments the phototherapy system comprises a light level controller. The light level controller may be housed within the base or base cover, and controls the power level or intensity of the light source, either controlling individual lights or the light source as a whole. The light level controller may be connected to a manual controller on the outside of the device, similar in position to the power switch 15, so that a caregiver can control the level of the lights, or the light level controller may be housed within the system and operates automatically based on temperatures sensors which sense the temperature of the system. In the later case, the light level controller comprises at least one temperature sensor that senses when the base cover becomes too warm for the patient's safety due to the light source emissions. Any reasonably suitable temperature sensor known to those skilled in the art may be used, for example, a thermocouple. When the sensor directly or indirectly senses the surface temperature of the base cover is greater than, for example, a threshold level programmed into a memory of the light level controller, the light source, either in its entirety or individual lights, will automatically shut off to prevent safety hazards to the patient. A fan, as will be described below as part of a cooling assembly, can also draw cool ambient air into and through the system and over the LEDs to cool them off by convection, and then vents can vent the warmed air out the vents of the system.

In preferred embodiments the system comprises a cooling assembly adapted to facilitate the removal of heat from the system. LEDs generate heat within the system, and as the system is enclosed around the LEDs, the heat has no way to efficiently exit the system and the patient may be in danger of exposure to such increases in heat. Therefore a thermal management system is required to ensure the safety of the patient. Natural convection thermal management techniques are well known in the art, and the system preferably comprises at least one fan to draw cooler ambient air into the system through vents 19 in the base, and draw the cool air over warmer system components such as the LEDs, where by convention the heat is transferred from the warmer components to the cooler air, and the warmed air is then vented out of the system through vents 14 as shown in FIG. 1, thus cooling the system. The cooling assembly may also comprise a temperature sensor, which may be the same temperature sensor as is used by the light level controller or it may comprise a different temperature sensor. Any reasonably suitable temperature sensor known to those skilled in the art may be used, for example, a thermocouple. In either case, when the sensor senses a temperature above a threshold temperature, for example, the cooling system may be automatically activated, turning on the fans which draw cool air into the system and cool the system down to an acceptable temperature. The cooling assembly can be activated in conjunction with the light level controller as described above.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A phototherapy system, comprising:
a rigid support surface adapted to support a patient without substantial deformation;
a light source disposed so as to transmit light through the support surface; and
the rigid support comprising adapted to permit light transmission from the light source through a first portion of the support surface and to limit light transmission from the light source through a second portion of the support surface.

2. The phototherapy system of claim 1 wherein the light source comprises a plurality of light-emitting diodes (LEDs).

3. The phototherapy system of claim 1 wherein the mask is further adapted to block light transmission from the light source through the second portion.

4. The phototherapy system of claim 1 wherein the mask is further adapted to alter light transmitted from the light source through the second portion.

5. The phototherapy system of claim 1 wherein the mask comprises a fluid-filled pad.

6. The phototherapy system of claim 5 wherein the fluid-filled pad comprises a transparent pouch filled with an opaque fluid; wherein the opaque fluid is adapted to displace away from the portion of the support surface supporting the patient such that there is a first region of the fluid-filled pad adapted to permit light transmission from the light source to the patient and a second region of the fluid-filled pad adapted to limit light transmission from the light source to the patient; wherein the first region has a first amount of opaque fluid, the second region has a second amount of opaque fluid, and the first amount is less than the second amount.

7. The phototherapy system of claim 5 wherein the fluid-filled pad comprises a transparent fluid and an opaque fluid; wherein the opaque fluid is adapted to displace away from the portion of the support surface supporting the patient such that there is a first region of the fluid-filled pad adapted to permit light transmission from the light source to the patient and a second region of the fluid-filled pad adapted to limit light transmission from the light source to the patient; wherein the first region consists substantially of transparent fluid and the second region consists substantially of opaque fluid.

8. The phototherapy system of claim 1 further comprising a patient orientation element.

9. The phototherapy system of claim 8 wherein the patient orientation element comprises a visible shape in or on the support surface.

10. The phototherapy system of claim 9 wherein the patient orientation element comprises an illustration of a patient.

11. The phototherapy system of claim 8 wherein the light source comprises a plurality of LEDs having a substantially non-uniform concentration with respect to the orientation element.

12. The phototherapy system of claim 8 wherein the patient orientation element has a head area adapted to orient the head of the patient with respect to the support surface.

13. The phototherapy system of claim 12 wherein the light source comprises a plurality of LEDs having a concentration greater near the head area than in another area of the orientation element.

14. The phototherapy system of claim 1 further comprising a pressure-sensitive switch adapted to control the light source.

15. The phototherapy system of claim 14 wherein the pressure-sensitive switch is coupled to a portion of the light source; and wherein the pressure-sensitive switch is activated by the patient's weight on a portion of the support surface and the pressure-sensitive switch thereby illuminates the corresponding portion of the light source.

16. The phototherapy system of claim 1 wherein the rigid support comprises a concave mattress.

17. A phototherapy system, comprising:
a support surface adapted to support a patient;
a light source disposed so as to transmit light through the support surface; and
a mask adapted to permit light transmission from the light source through a first portion of the support surface and to limit light transmission from the light source through a second portion of the support surface;
wherein the mask comprises thermochromic material.

18. The phototherapy system of claim 17 wherein the thermochromic material has a first region adapted to permit light transmission from the light source through a first portion of the support surface and a second region adapted to limit light transmission from the light source through a second portion of the support surface; wherein the first region has a first temperature, the second region has a second temperature, and the first temperature is greater than the second temperature.

19. A phototherapy system, comprising:
a support surface adapted to support a patient;
a light source disposed so as to transmit light through the support surface; and
a mask adapted to permit light transmission from the light source through a first portion of the support surface and to limit light transmission from the light source through a second portion of the support surface;
wherein the mask comprises a patient location sensor.

20. The phototherapy system of claim 19 further comprising a light level controller.

21. The phototherapy system of claim 20 wherein the patient location sensor is adapted to sense the location of the patient on the support surface and communicate the location of the patient to the light level controller; and wherein the light level controller is adapted to illuminate a portion of the light source that corresponds substantially to the location of the patient on the support surface.

22. The phototherapy system of claim 19 wherein the patient location sensor comprises a pressure-sensitive switch coupled to a portion of the light source.

23. The phototherapy system of claim 22 wherein the pressure-sensitive switch is activated by the patient's weight on a portion of the support surface and the pressure-sensitive switch thereby illuminates the corresponding portion of the light source.

* * * * *

UNITED STATES PATENT AND TRADEMARK OFFICE
CERTIFICATE OF CORRECTION

PATENT NO.        : 8,048,136 B2
APPLICATION NO.   : 11/423694
DATED             : November 1, 2011
INVENTOR(S)       : Dong-Chune C. Chung et al.

It is certified that error appears in the above-identified patent and that said Letters Patent is hereby corrected as shown below:

The sheet of drawing consisting of Figure 7 should be deleted to appear as per attached Figure 7.

Signed and Sealed this
Seventeenth Day of July, 2012

David J. Kappos
*Director of the United States Patent and Trademark Office*